United States Patent [19]

Tanaka et al.

[11] Patent Number: 4,663,048

[45] Date of Patent: May 5, 1987

[54] METHOD FOR THE SEPARATION OF A BASIC AMINO ACID FROM ITS FERMENTATION BROTH

[75] Inventors: Kiyoshi Tanaka, Tokyo; Yoshihiro Koga, Saga; Masaru Saeki, Fujisawa; Tetsuya Kaneko, Kawasaki; Tetsuya Kawakita, Yokohama, all of Japan

[73] Assignee: Ajinomoto Co., Inc., Tokyo, Japan

[21] Appl. No.: 713,857

[22] Filed: Mar. 20, 1985

[30] Foreign Application Priority Data

Mar. 31, 1984 [JP] Japan .................................. 59-64338

[51] Int. Cl.$^4$ .............................................. B01D 13/00
[52] U.S. Cl. .................................... 210/638; 210/639; 210/651; 210/259
[58] Field of Search ............... 210/638, 639, 651, 259; 127/48, 55

[56] References Cited

U.S. PATENT DOCUMENTS

4,432,806 2/1984 Madsen et al. ................. 210/639 X
4,523,999 6/1985 Toyoshi et al. ................ 210/651 X Primary Examiner—Frank Spear
Attorney, Agent, or Firm—Oblon, Fisher, Spivak, McClelland & Maier

[57] ABSTRACT

A method for separating a basic amino acid from its fermentation broth, or the liquid resulting from the intermediate treatment of the fermentation broth, containing high-molecular weight contaminants which entails permeating the broth, or liquids resulting from the intermediate treatment of the broth, through a semipermeable membrane, until the basic amino acid is separated from the high-molecular weight contaminants, by passing through the membrane in the permeate; contacting the permeate with a strongly acidic cation exchange resin; and eluting the adsorbed basic amino acid from the cation exchange resin.

13 Claims, 17 Drawing Figures

EFFLUENT

FIG. 16

EFFLUENT

FIG. 17

METHOD FOR THE SEPARATION OF A BASIC AMINO ACID FROM ITS FERMENTATION BROTH

BACKGROUND OF THE INVENTION

1. Field of the Invention

The present invention relates to a method for greatly reducing the amount of water used in a cation exchange resin treatment for the separation of a basic amino acid from its fermentation broth.

2. Description of the Prior Art

Basic amino acids are widely used as feedstuffs and medicines, for example. At present, basic amino acids are mainly produced by fermentation, and cation exchange resins are generally utilized for separating basic amino acids from their fermentation broths. This cation exchange resin treatment generally entails an adsorption step in which a fermentation broth adjusted to a definite pH is brought into contact with strongly acidic salt-type cation exchange resins such as $NH_4^+$-type one to adsorb the basic amino acid thereonto and, an elution step in which the basic amino acid is eluted with an eluting agent such as ammonia water, and a regeneration step wherein the cation exchange resin is regenerated to salt type one. By repeating the adsorption and elution steps as one cycle, basic amino acids are separated from their fermentation broths.

One of the problems of using the cation exchange resin treatment is that a very large quantity of water is required. In particular, a fermentation broth is passed through a cation exchange resin layer and then a washing water feed is employed in order to completely pass the fermentation broth through the cation exchange resin layer at the adsorption step. Further, at the elution step, a washing water feed is employed in order to completely pass the eluting agent. Additionally, suspensions and the like, contained in the fermentation broth, accumulate in the cation exchange resin layer at the adsorption step, and a large quantity of water must be used to remove the accumulated solid. Hence, there are problems relating not only to the amount of water consumed but also to the increased amount of waste water discharged.

Various methods for reducing the amount of washing water used have been investigated and, some methods for substituting various waste liquids for a part of this washing water have been developed (Japanese Unexamined Patent Publications No. 127879/75, 11173/77, etc.). However, due to mixing with liquids used in subsequent steps or the loss of basic amino acids in elution by washing water, which occur in these methods, a considerable quantity of fresh washing water must still be used.

Moreover, the concentration of the basic amino acids in the eluate discharged from the cation exchange resin is low and, therefore, much energy is required for concentrating the eluate.

Therefore, a need clearly continues to exist for a method for separating a basic amino acid from its fermentation broth, or the liquids resulting from the intermediate treatment of the fermentation broth, containing high-molecular weight contaminants, using a cation exchange resin, which utilizes a greatly reduced amount of water, and which, therefore, also requires the use of less energy in concentrating large quantities of eluate.

SUMMARY OF THE INVENTION

Accordingly, it is an object of the present invention to provide a method for separating a basic amino acid from its fermentation broth, or the liquids resulting from the intermediate treatment thereof, using a cation exchange resin, which utilizes a greatly reduced amount of water, and which, therefore, also requires the use of less energy in concentrating large quantities of eluate.

It is also an object of this invention to provide a method for separating a basic amino acid from its fermentation broth, or the liquids resulting from the intermediate treatment thereof, using a cation exchange resin, which utilizes a greatly reduced amount of energy as it is now unnecessary to concentrate large quantities of eluate.

According to the present invention, the foregoing and other objects are attained by providing a method for separating a basic amino acid from its fermentation broth or the liquids resulting from the intermediate treatment of said fermentation broth, containing high-molecular weight contaminants, which entails permeating a fermentation broth of a basic amino acid, or the liquids resulting from the intermediate treatment of the fermentation broth, through a semi-permeate membrane, until the basic amino acid is separated from the high-molecular weight contaminants by passing through said membrane in the permeate; contacting said permeate with a strongly acidic cation exchange resin, and eluting the adsorbed basic amino acid from the cation exchange resin.

DETAILED DESCRIPTION OF THE PREFERRED EMBODIMENT

According to the present invention, it is now possible to greatly reduce the amount of water used in the cation exchange treatment method for the separation of a basic amino acid from its fermentation broth.

The fermentation broths of basic amino acids to which the method of the present invention applies include fermentation broths of, for example, lysine, arginine, and ornithine which have been fermentatively produced from beet molasses, cane molasses, or starch hydrolysate or a mixture thereof as carbon sources. Regardless of the type of carbon source used, the amount of washing water required, according to the conventional methods is quite large, particularly in the case of fermentation broths made from carbon sources having low purity such as beet molasses, and cane molasses, and, therefore, the method of the present invention is particularly useful as a method for separating basic amino acids from such fermentation broths. Of course, the present method may be used to separate any basic amino acid from a fermentation broth from any carbon source.

The intermediate treatment liquids include solutions of basic amino acids at various treatment steps obtained until the desired basic amino acids are separated and obtained from the fermentation broths. These intermediate treatment liquids contain high molecular contaminants which are to be removed by a semi-permeable membrane, for example, bacteria, humin, proteins, gums, polysaccharides or pigments. Examples of the intermediate treatment liquids include solutions obtained by subjecting bacteria, or proteins, for example, in fermentation broths to coagulation or solidification treatment and solutions obtained after various conventional treatments.

The semi-permeable membrane is a membrane through which basic amino acids are permeated but the aforesaid high molecular weight contaminants are not permeated and, includes such membranes as a membrane for ultrafiltration, a membrane for fine microfiltration, or a reverse osmosis membrane having a low rejection rate called "loose RO", for example. Materials for membranes are not particularly limited but materials for membranes for ultrafiltration are exemplified by polyacrylonitrile, or polysulfone, for example, materials of membranes for microfiltration by polyvinyl alcohol, for example; and materials of low rejection rate reverse osmosis membranes by cellulose acetate, or polybenzimidazolone, for example. The module configuration of semi-permeable membranes may be conventional, i.e., a tubular form, a flat-sheet form, a spiral wound form, or a hollow fiber form, for example. Any commercially available device may be used as it is, for mounting such a semi-permeable membrane.

It is preferred that the pH is adjusted to about 2 to 5 prior to treating a fermentation broth of a basic amino acid or an intermediate treatment liquid with a semi-permeable membrane. By this pH adjustment, high molecular weight contaminants can be coagulated to enhance the removal of these contaminants at the semi-permeable membrane step, while improving the permeation flow rate. This is because a fermentation broth of a basic amino acid or an intermediate treatment liquid contains various high molecular weight impurities such as bacteria, pigments, humin, gums, polysaccharides, and proteins. Considerable parts of these high molecular impurities such as humin and some kinds of pigments, contain carboxyl groups. The adjustment of pH in the aforesaid range results in a charge-free state of the high molecular weight impurities having carboxyl groups to reduce affinity with water, whereby the impurities will precipitate. Acids and alkalis used for the pH adjustment may be conventional ones. Examples of the acids include mineral acids such as hydrochloric acid, sulfuric acid, nitric acid, and phosphoric acid; or organic acids such as acetic acid. Examples of the alkalis include sodium hydroxide, potassium hydroxide, lime, and ammonia.

To confirm the effect of the pH adjustment, the following experiment was performed and the results are shown below. This example is, of course, provided for purposes of illustration only and is not intended to limit the present invention.

The experiment comprises subjecting a lysine fermentation broth (pH 7.0) obtained by using beet molasses as the carbon source to ultrafiltration using a hollow fiber type ultrafiltration module (cut-off molecular weight of the membrane, 6,000) made of polyacrylonitrile, as it was or after adjusting the pH of the lysine fermentation broth to 3.0.

| pH Adjustment | Rate of Removing High Molecular Weight Impurities | Rate of Removing Pigment |
|---|---|---|
| pH 3.0 | 50% | 63% |
| no adjustment (pH 7.0) | 30% | 37% |

By adjusting the pH from 7.0 to 3.0 as shown in the table, the rate of removing high molecular weight impurities and the rate of removing pigments are improved by 67% and 70%, respectively.

The conditions for permeation may be conventional and, temperature, pressure and other conditions are determined, taking properties of the fermentation broth of basic amino acids or the intermediate treatment liquids into account.

Next, the semi-permeable membrane permeate is brought into contact with a strongly acidic cation exchange resin. By adjusting the pH of the semipermeable membrane permeate to a range in which the basic amino acid is present as monovalent cations, in the case of the contaminant inorganic cations in a low concentration, and, in the case of the contaminant inorganic cations in a high concentration, by adjusting the pH of the permeate to a range wherein the basic amino acids are present as bivalent cations, e.g., pH of approximately 2 to 4, the amount of the basic amino acid adsorbed can be increased. Needless to say, the pH need not be adjusted when the pH of the semi-permeable membrane permeate is in such a suitable pH range.

The types of the strongly acidic cation exchange resins which can be used are not particularly limited but, for example, DIAION SK-1B, Amberlites IR-120, IR-122 and XE-100, DOWEX 50, Duolites C-25 and C-20, Permchit Q (all are trademarks), etc. may be appropriately used. The salt types of cation exchange resins, which are well-known, are not particularly limited but, $NH_4^+$-type, $Na^+$-type, $K^+$-type, etc. may be appropriately selected in relation to an eluting agent and/or a regenerating agent. However, $NH_4^+$-type is generally preferred.

The operational procedure for the cation exchange resin treatment may be conducted according to the prior arts method. However, by the use of the method newly devised by the present inventors, the quantity of water used can be surprisingly reduced.

Figure 1:
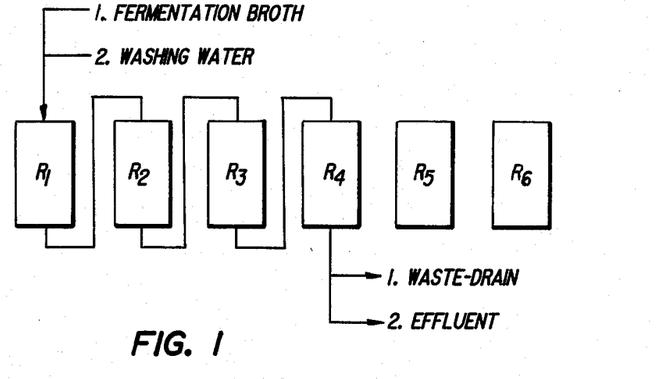
FIG. 1 illustrates a conventional 4-tower adsorption and 3-tower elution system.

In order to clarify the present invention, an example of a conventional "4-tower-adsorption and 3-tower-elution system" will now be explained by reference to FIGS. 1–6. The cation exchange resin towers are used as 6 towers $R_1$, $R_2$, $R_3$, $R_4$, $R_5$ and $R_6$ as can be seen in FIG. 1. After towers $R_1$, $R_2$, $R_3$ and $R_4$ are combined in series as illustrated in FIG. 1, from tower $R_1$ is fed a fermentation broth and then washing water. From tower $R_4$ is discharged, first, a liquid having a low concentration of impurities such as inorganic ions (hereinafter referred to as "Waste-Drain") and then a solution high in concentration of impurities (hereinafter referred to as "Effluent").

Figure 2:
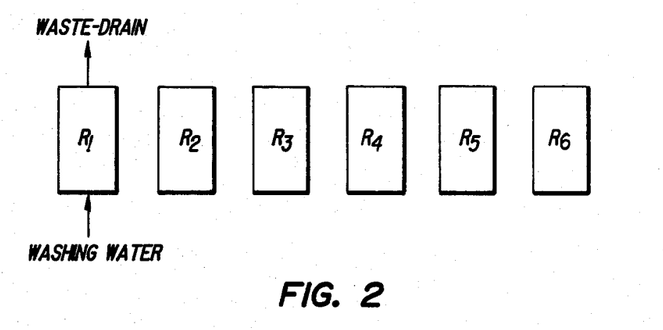
FIG. 2 illustrates the backwashing of the first tower of the conventional system of FIG. 1.

Tower $R_1$ is then subjected to back-washing as is illustrated in FIG. 2. The discharged solution is classified as Waste-Drain according to its concentration of impurities.

Figure 3:
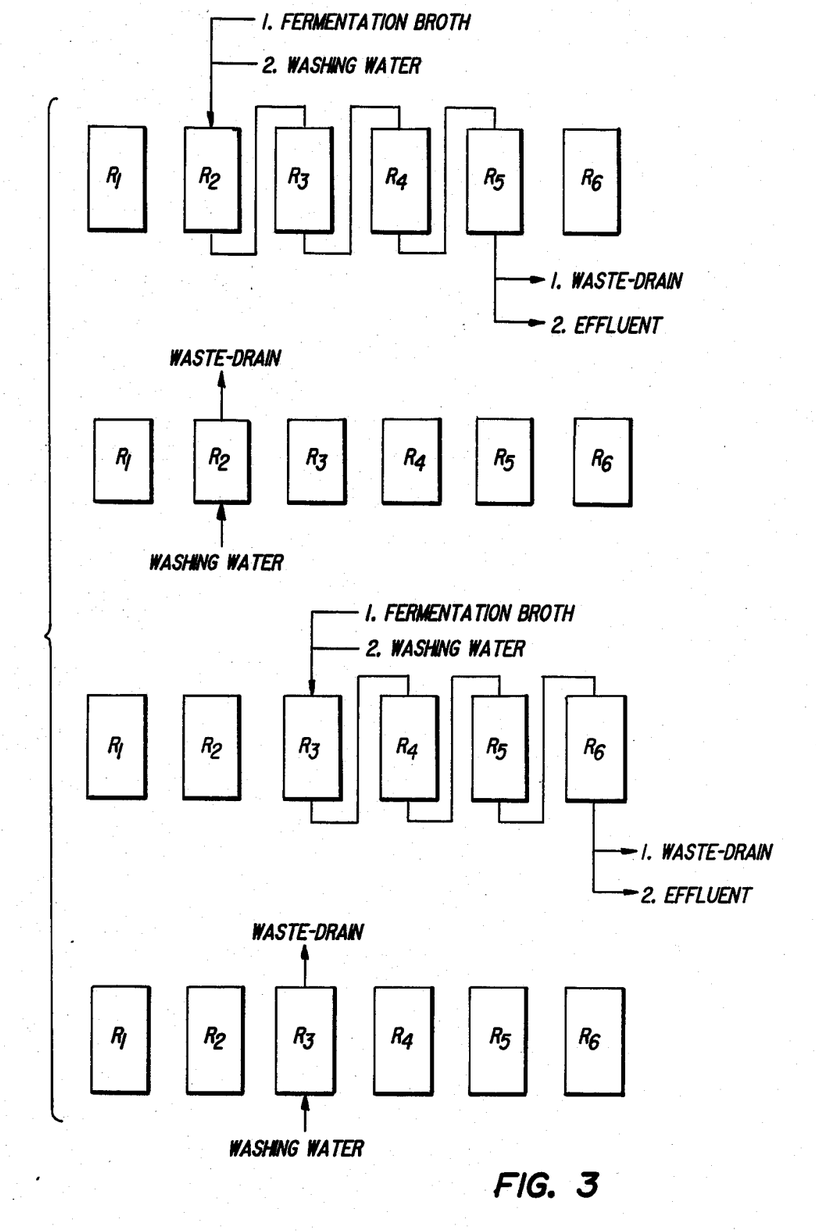
FIG. 3 illustrates the processes conducted using the conventional systems of FIGS. 1 and 2 in repetition.

The above-mentioned process is repeated twice more by shifting the towers one by one, as illustrated in FIG. 3.

Figure 4:
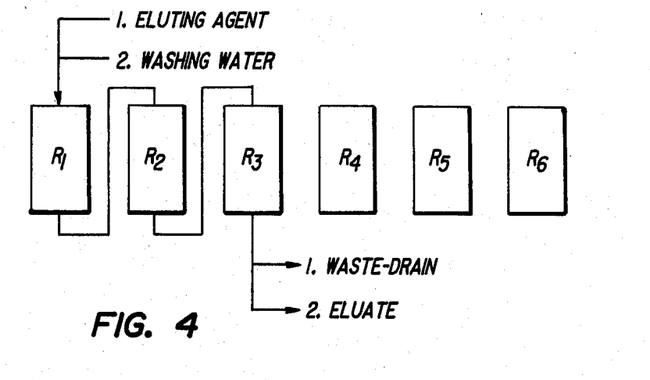
FIG. 4 illustrates the elution step after combining 3-towers in series according to the conventional system.

After towers $R_1$, $R_2$ and $R_3$ are combined in series, an eluting agent is fed from tower 1 and then washing water as illustrated in FIG. 4. From tower $R_3$ is discharged, first, Waste-Drain, and then an eluate containing the basic amino acid.

Figure 5:
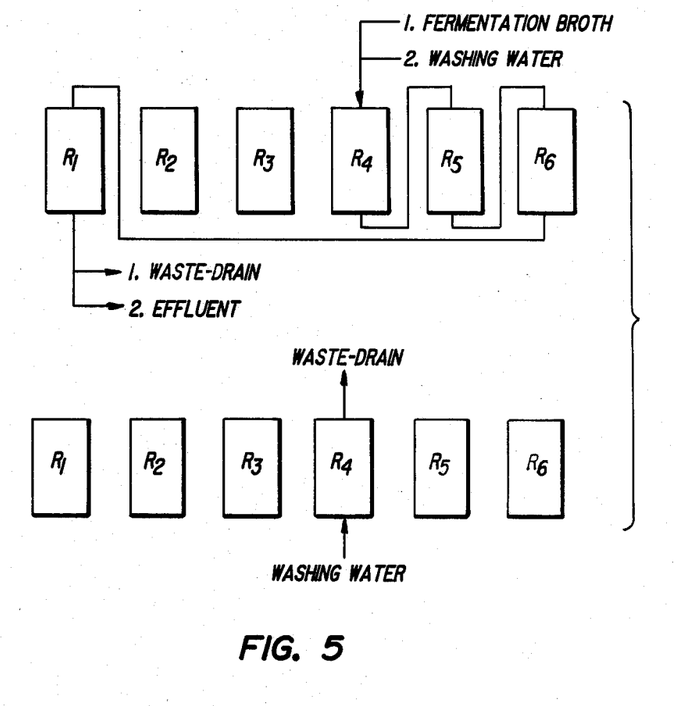
FIG. 5 illustrates the adsorption step after combining 4-towers in series according to the conventional system.
Figure 6:
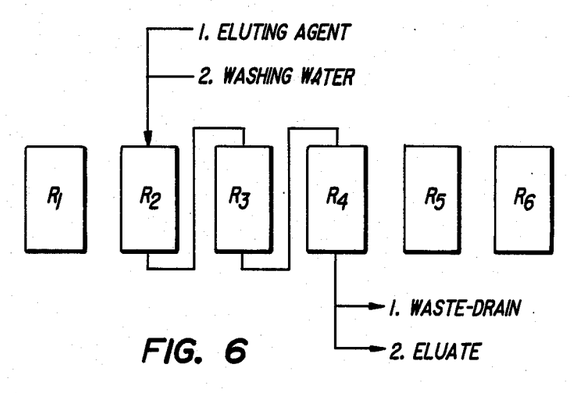
FIG. 6 illustrates the elution step, combining 3-towers in series, by eluting and washing, in the conventional system.

After towers $R_4$, $R_5$, $R_6$ and $R_1$ are combined in series, from tower $R_4$ is fed, first, a fermentation broth and then washing water as illustrated in FIG. 5. Then, after towers $R_2$, $R_3$ and $R_4$ are combined in series, from tower $R_2$ is fed an eluting agent and then washing water as illustrated in FIG. 6.

It is noted that the adsorption step and then the eluting step are repeated by shifting the towers one by one. For clarity, it is, again, noted that the above discussion relates to the conventional technique.

By contrast, the present method has the predominant characteristic of dividing the solution discharged in the elution step into three fractions (using lysine as an example): a fraction without lysine (hereinafter referred to also as "Waste-Drain"), a fraction low in concentration of lysine (hereinafter referred to as "Pre-eluate") and fraction high in concentration of lysine (hereinafter referred to as "High-concentration Eluate"), and in using this Pre-eluate as washing water for adsorption step. Namely, this increases the lysine concentration in the eluate and eliminates the use of fresh water as washing water in the adsorption step. In addition, this method saves water by making the best use of solutions discharged in respective steps from resin layers according to their characteristics, and minimizes the quantity of water used, for example by: use of a fraction discharged in the stage of washing in the preparatory step for adsorption (hereinafter referred to as "Recovered Water") as washing water for the elution step of a succeeding cycle; disuse of back-washing in the adsorption step through submitting in advance a fermentation broth or intermediate treatment liquid to semi-permeable membrane treatment; use of Effluent for homogenizing treatment to prevent a resin layer from channeling; use of a fraction without lysine discharged in the elution step (hereinafter referred to as "Non-lysine Fraction") as washing water in the adsorption step.

This new resin treatment method will now be explained first on a single-tower system.

Figure 7:
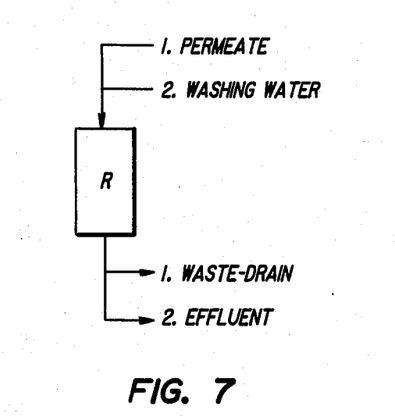
FIG. 7 illustrates a single tower adsorption step according to the present invention.

FIG. 7 shows a single tower adsorption step according to the present invention. To the cation exchange resin tower (R) is fed a permeate through a semi-permeable membrane, then the tower is washed with water. This tower is not subjected to back-washing.

Figure 8:
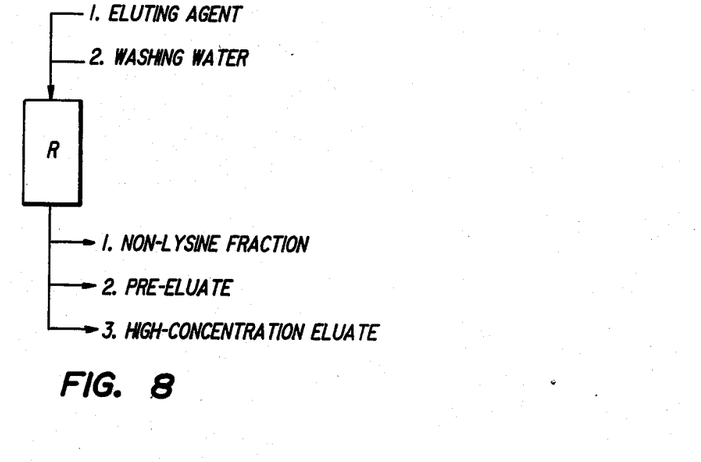
FIG. 8 illustrates a single tower elution step according to the present invention.

FIG. 8 shows a single tower elution step according to the present invention, wherein to the cation exchange resin tower is fed an eluting agent and then the tower is washed with water.

From the tower is discharged a Non-lysine fraction and then an eluate fraction containing a basic amino acid. This eluate fraction is separated into Pre-eluate and High-concentration Eluate. From the High-concentration Eluate, the basic amino acid is obtained by an ordinary process, and the Pre-eluate is used as washing water in the adsorption step of a succeeding cycle. The switching point in collection between the High-concentration Eluate and Pre-eluate is set suitable according to the necessity. That is to say, if a great amount of a basic amino acid is wanted to be obtained by one operation, the quantity of Pre-eluate is to be reduced, while, if the higher concentration of the basic amino acid in High-concentration Eluate is preferable, the quantity of Pre-eluate is to be increased.

Preparatory Step for Adsorption

Figure 9:
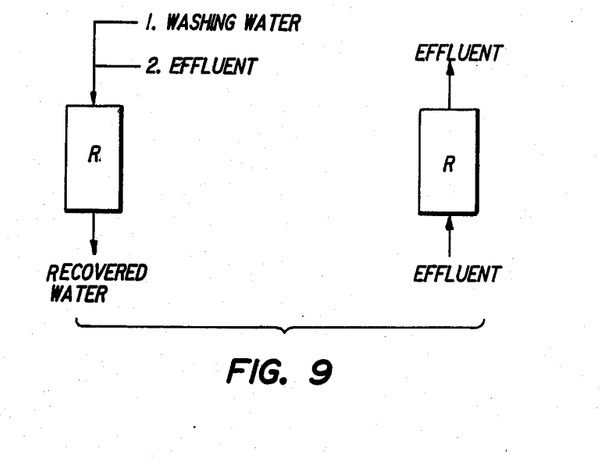
FIG. 9 illustrates the preparatory step for adsorption according to the present invention.

FIG. 9 shows the preparatory step for adsorption according to the present invention. It should be noted that, according to conventional methods, this step is carried out by increasing the amount of washing water at the elution step, but to reduce the quantity of washing water, this step is added according to the present invention.

First, is fed washing water and then Effluent obtained in the adsorption step, to eliminate alkalis in the resin layer. Recovered water discharged from the tower is used as washing water in the elution step of a succeeding cycle. The resin layer is, if necessary, homogenized further with Effluent to prevent channeling in a succeeding process.

Adsorption Step

Figure 10:
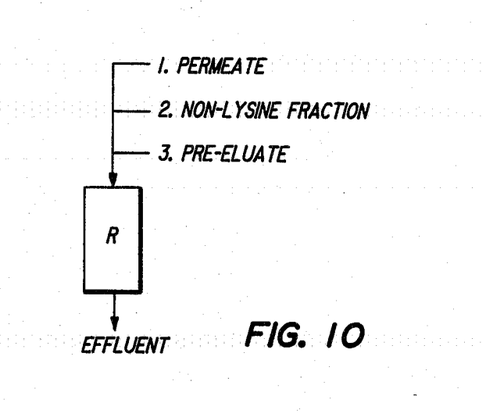
FIG. 10 illustrates a single tower adsorption step according to the present invention.

FIG. 10 illustrates a single tower adsorption step according to the present invention.

First, a permeate obtained through a semi-permeable membrane is fed to the tower, followed by a non-lysine fraction, and then by the pre-eluate of a preceding cycle as washing water. A solution discharged from the tower is only a liquid classified as Effluent.

Elution Step

Figure 11:
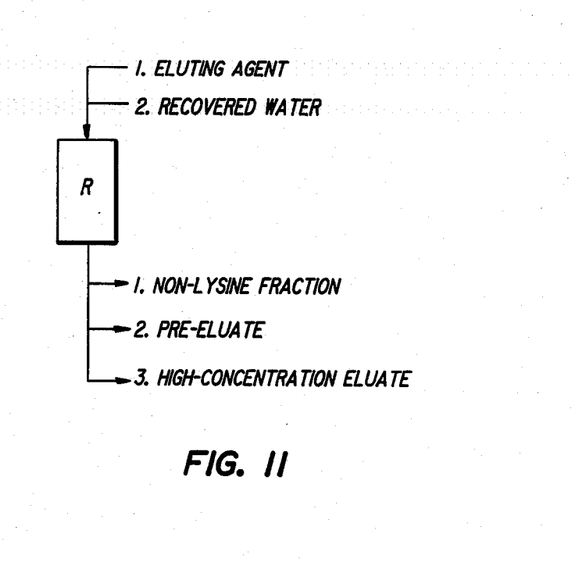
FIG. 11 illustrates a single tower elution step according to the present invention.

FIG. 11 illustrates a single tower elution step according to the present invention.

In this step, an eluting agent, and then water recovered in the preparatory step for adsorption is fed to the tower. As to discharged liquids, their discharge is made in the following order: the liquid classified as non-lysine fraction; pre-eluate and high-concentration eluate.

Preparatory Step for Adsorption

This step is essentially conducted as described above for FIG. 9.

Stationary operation is carried out by combining the above-mentioned steps, a, b, c as one cycle. The quantity of fresh water used in this process is minimized, and the quantity of waste liquids discharged outside the system is reduced to a great extent.

Now, the use of the multi-tower process, according to the present invention, will now be described. The following discussion refers to the use of a 4-tower adsorption and 3-tower elution system. Of course, this only will serve to exemplify the present invention and is not to be construed as limiting the same.

Adsorption Step

Figure 12:
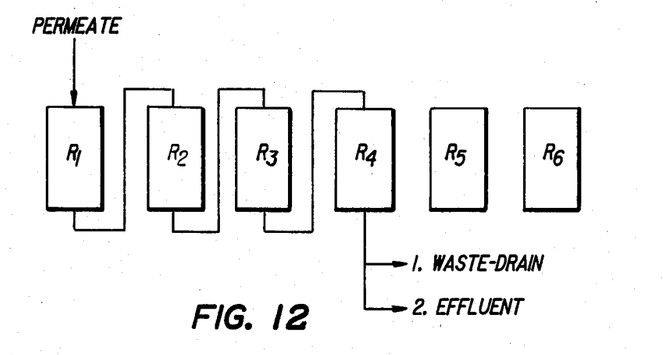
FIG. 12 illustrates a 4-tower adsorption step according to the present invention.

FIG. 12 illustrates the 4-tower adsorption step according to the present invention.

After towers, $R_1$, $R_2$, $R_3$ and $R_4$ are combined in series, a permeate is fed from tower $R_1$. From tower $R_4$ is discharged the Waste-Drain and Effluent.

Figure 13:
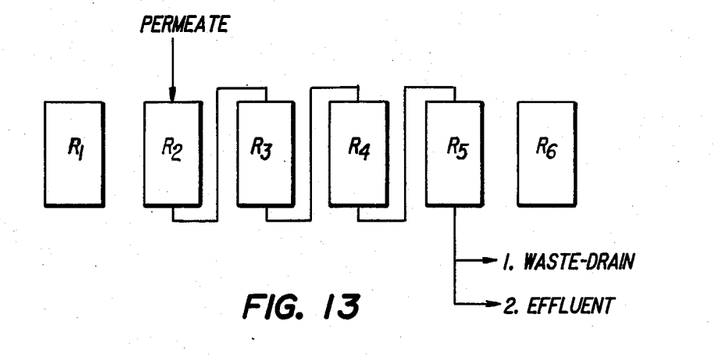
FIG. 13 illustrates the feeding of permeate from tower 2, with waste-drain and discharge of effluent from tower 5, according to the present invention.

After towers $R_2$, $R_3$, $R_4$ and $R_5$ are combined in series, a permeate is fed from tower $R_2$. From tower $R_5$ is discharged the Waste-Drain and Effluent. This is illustrated in FIG. 13.

Figure 14:
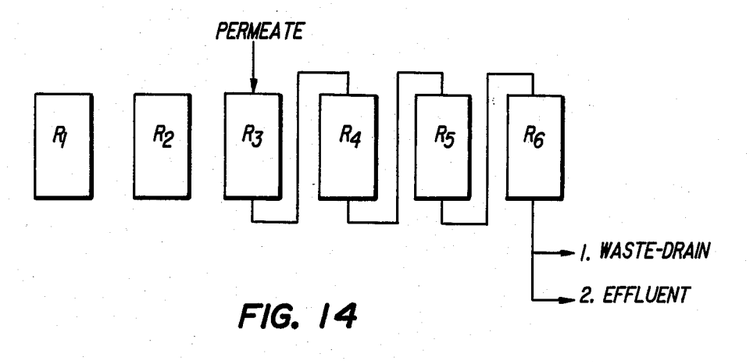
FIG. 14 illustrates the feeding of permeate from tower 3 with waste-drain and discharge of effluent from tower 6, according to the present invention.

After towers $R_3$, $R_4$, $R_5$ and $R_6$ are combined in series, a permeate is fed from tower $R_3$. From tower $R_6$ is discharged Waste-Drain and Effluent. This is illustrated in FIG. 14.

Elution Step

Figure 15:
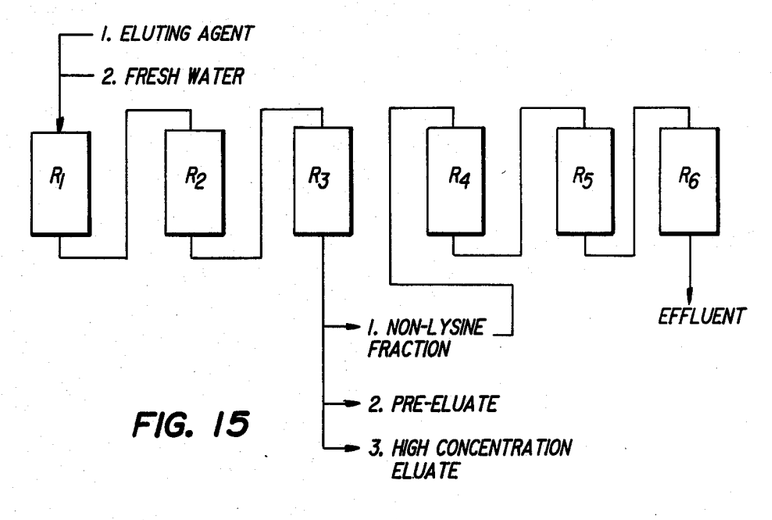
FIG. 15 illustrates a 3-tower elution step according to the present invention.

FIG. 15 illustrates a 3-tower elution step according to the present invention.

After towers $R_1$, $R_2$ and $R_3$ are combined in series, from tower $R_1$ is fed an eluting agent and then the tower is washed with fresh water. From tower $R_3$ is discharged first a liquid classified as non-lysine fraction. This non-lysine fraction is fed to tower $R_4$ after towers $R_4$, $R_5$ and $R_6$ are combined in series. From tower $R_6$, Effluent is discharged. Then, preeluate is discharged from tower $R_3$. It is collected and used as washing water for the adsorption step of a succeeding cycle. Finally, from tower $R_3$, is discharged High-concentration Eluate, from which the basic amino acid may be obtained in a conventional manner.

Preparatory Step for Adsorption

To tower $R_1$ is applied the same step as that illustrated in FIG. 9.

Adsorption Step

Figure 16:
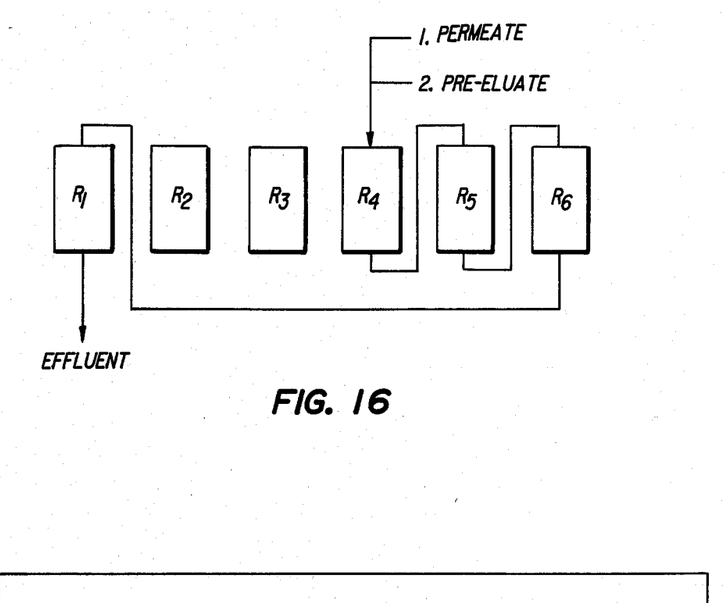
FIG. 16 illustrates a 4-tower adsorption step according to the present invention.

After towers $R_4$, $R_5$, $R_6$ and $R_1$ are combined in series, from tower $R_4$ is fed a permeate and then a preeluate of a preceding cycle as washing water. From tower $R_1$ is discharged Effluent. This is illustrated in FIG. 16.

Elution Step

Figure 17:
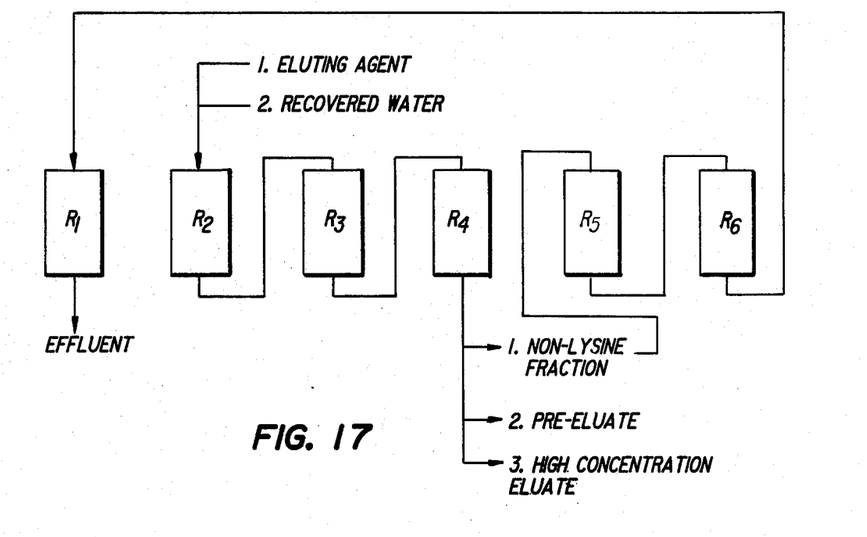
FIG. 17 illustrates a 3-tower elution step according to the present invention.

FIG. 17 illustrates a 3-tower elution step according to the present invention.

After towers $R_2$, $R_3$ and $R_4$ are combined in series, from tower $R_2$ is fed an eluting agent and then recovered water in a preceding cycle, as washing water. While the non-lysine fraction is discharged from tower $R_4$, towers $R_5$, $R_6$ and $R_1$ are combined in series with tower $R_4$. When the non-lysine fraction is turned into pre-eluate and collected from tower $R_4$. The High-concentration Eluate is also collected from tower $R_4$.

Preparatory Step for Adsorption

To tower $R_2$ is applied the same step as that illustrated in FIG. 9.

The above-mentioned steps are repeated as one cycle, while shifting the towers one by one.

The method of the present invention is characterized by using, as washing water, various kinds of liquids discharged from the cation exchange resin towers, through submitting fermentation broths or intermediate treatment liquids to semi-permeable membrane treatment prior to the cation exchange resin treatment thereby succeeding in great reduction of water used in the cation exchange resin step.

Particularly by adjusting the pH of a fermentation broth or intermediate treatment liquids to a pH of about 2 to 5 prior to the permeation treatment using a semi-permeable membrane, the rate of removing the high molecular weight impurities can be improved through the permeation treatment and at the same time, the rate of permeation can be enhanced to render the treatment easy. Further, by using the aforesaid, novel operation of the cation exchange resin treatment developed by the present inventors, the quantity of water used at the cation exchange resin treatment can be minimized and at the same time, the concentration of the basic amino acid in the eluate can be greatly enhanced and the load on energy for the subsequent concentration can be reduced. Benefits obtained thereby are not only reduction in the quantity of water used and of energy consumption but also miniaturization of equipments. Accordingly, fixed costs can be reduced and other various benefits are accompanied.

The present invention will now be further illustrated by certain examples and references which are provided for purposes of illustration only and are not intended to limit the present invention.

EXAMPLE

A lysine fermentation broth (pH 7.0) obtained using beet molasses as the carbon source was subjected to ultrafiltration using a hollow-fiber type ultrafiltration membrane (cut-off molecular weight: 50,000) made of polyacrylonitrile. The rate of removing pigments and the rate of removing soluble proteins in the permeate were 17% and 9%, respectively. The rate of the removing pigments was determined by measuring absorbance at 400 nm. The rate of removing soluble proteins was determined by measurement in accordance with the Lowly-Folin method.

The permeate having a lysine concentration of 7.4 g/dl was adjusted to pH of 2 using sulfuric acid.

As cation exchange resin towers were employed 6 towers in each of which 1.5 liters of strongly acidic cation exchange resin Duolite C-20, $NH_4^+$-type, was packed.

The operational procedure was performed in a manner similar to the procedures described hereinabove. At the adsorption step in the starting operation, 4.5 liters of a permeate was fed at a flow rate of 3.0 l/hr and the separation of Waste-Drain and Effluent was switched at pH 5, in the case of towers $R_1$ to $R_4$. In the case of towers $R_2$ to $R_5$ and $R_3$ to $R_6$, 3.0 liters of the permeate were fed at a flow rate of 3.0 l/hr to obtain 0.5 liter of Waste-Drain and then 2.5 liters of Effluent. At the elution step in the starting operation, in the case of towers $R_1$ to $R_3$, 3.0 liters of 4N ammonia water as an eluting agent and then 1.1 liter of pure water as washing water were fed both at a rate of 1.5 l/hr. The initially eluted liquid (Non-lysine Fraction), 2.9 liters, was fed to towers $R_4$ to $R_6$ and 2.9 liters of Effluent was collected from tower $R_6$. Next, the Pre-eluate eluted from tower $R_3$ was 0.8 liter (fraction having a lysine concentration of 1 to 18 g/dl) and the average lysine concentration was 9 g/dl. In this example, fractions having a lysine concentration of 18 g/dl or more were collected as High-concentration Eluate. The amount of this eluate was 0.4 liter and the lysine concentration was 25 g/dl. The quantity of washing water was 0.6 liter at the preparatory step for adsorption and washing water and fed at a flow rate of 3.0 l/hr/. Subsequently, 0.5 liter of Effluent was also fed at a flow rate of 3.0 l/hr to obtain 1.1 liter of Recovered Water. The quantity of the Effluent used for homogenization for purpose of preventing channeling was 0.7 liter. The Effluent was introduced from the bottom of the resin tower at 4.5 l/hr (homogenization) and then recollected about 0.7 liter.

The quantity of the permeate fed at each cycle in stationary operations was 3.0 liters; 0.6 liter of the Pre-eluate was used as washing water. In any case, the feed rate was 3.0 l/hr, whereby 3.6 liters of Effluent was collected at each cycle. As the eluting agent, 0.8 liter of 4N ammonia water was used and, 1.1 liter of Recovered Water was used as washing water. In any case, the feed rate was 1.5 l/hr. At each cycle, 0.6 liter of Non-lysine Fraction, 0.6 liter of Pre-eluate and 0.7 liter of High-concentration Eluate were collected. The lysine concentration of Pre-eluate was 8 g/dl and the lysine concentration of High-concentration Eluate was 22 g/dl. The conditions for the preparatory step for adsorption were the same as in the starting operation.

Next, for the purpose of comparison, the same lysine fermentation broth was adjusted to a lysine concentration of 7.4 g/dl at pH 2 and then subjected to the aforesaid cation exchange resin treatment in the prior art. The same cation exchange resin towers were used, and the quantity of the fermentation broth at each cycle was the same as the aforesaid method. As the eluting agent, 1.3 liter (2.0 liters at the first cycle) of 2N ammonia water was used. As washing water at the adsorption step, 2.0 liters of fresh water was used at each cycle. Thus, 1.0 liter of Waste-Drain and 4.0 liters (5.5 liters at the first cycle) of Effluent were collected. As washing water for back-washing at the adsorption step, 5.0 liters of fresh water was used. Washing water was fed from the bottom of the resin tower at 4.5 l/hr and, 5.0 liters of Waste-Drain was withdrawn. As washing water at the elution step, 2.2 liters of fresh water was used, whereby 2.1 liters (2.7 liters at the first cycle) of Waste-Drain and 1.4 liter (1.5 liter at the first cycle) of the eluate having a lysine concentration of 12 g/dl were collected at each cycle.

Thus, the stationary operations according to the prior arts method and this invention were repeated by 10 cycles. The results (average in 10 cycles) obtained are shown below.

|  | This Invention | Prior Arts Method |
| --- | --- | --- |
| Amount of eluate | 0.7 l | 1.4 l |
| Amount of other liquids discharged | 4.2 l | 12.1 l |
| Lysine concentration of eluate | 22 g/dl | 12 g/dl |
| Amount of fresh water used | 0.6 l | 9.2 l |

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for separating a basic amino acid from its fermentation broth, or the liquid resulting from the intermediate treatment of said fermentation broth, containing high-molecular weight contaminants, which comprises:
    (a) permeating a fermentation broth, or the liquids resulting from the intermediate treatment of said fermentation broth, through a semi-permeable membrane, until the basic amino acid is separated from the high-molecular weight contaminants, by passing through said membrane of the permeate;
    (b) contacting said permeate with a strongly acidic cation exchange resin;
    (c) eluting the absorbed basic amino acid from the cation exchange resin; and
    (d) dividing the solution discharged in the elution step into three fractions;
        (i) a fraction without amino acid therein,
        (ii) a fraction having a low concentration of amino acid therein, and
        (iii) a fraction having a high concentration of amino acid therein, and wherein said fraction (ii) having a low concentration of amino acid therein is used as washing water for the adsorption step (b).

2. the method for separating a basic amino acid according to claim 1, which further comprises adjusting the pH of the fermentation broth, or the liquids resulting from the immediate treatment of said fermentation broth, to a pH of about 2-5 prior to permeating said broth or resulting liquids through the semi-permeable membrane.

3. The method for separating a basic amino acid according to claim 2, wherein the fermentation broth is adjusted to a pH of 3.0.

4. The method for separating a basic amino acid according to claim 1, wherein most of the liquid discharged, during the treatment of the permeate with the strongly acidic cation exchange resin treatment, from a cation exchange resin layer during an adsorption step or during an elution step, or during both, is reused as water to wash the cation exchange resin layer.

5. The method for separating a basic amino acid according to claim 1, wherein said fermentation broth is a fermentation broth of lysine, arginine or ornithine which has been fermentatively produced from beet molasses, cane molasses or starch hydrolysate or a mixture thereof.

6. The method for separating a basic amino acid according to claim 1, wherein said intermediate treatment liquid comprises solutions obtained by subjecting bacteria, proteins, humin, gums or polysaccharides or a mixture thereof, in a fermentation broth to coagulation or solidification treatment.

7. The method for separating a basic amino acid according to claim 1, wherein said semi-permeable membrane is selected from the group consisting of membranes for ultrafiltration, membranes for fine microfiltration and reverse osmosis membranes having a low rejection rate.

8. The method for separating a basic amino acid according to claim 1, wherein said semi-permeable membrane has a tubular, a flat-sheet, a spiral wound or a hollow fiber form.

9. The method for separating a basic amino acid according to claim 1, wherein said strongly acidic cation exchange resin is a salt-type cation exchange resin selected from the group consisting of $NH_4^+$-type. $Na^+$-type or $K^+$-type.

10. The method for separating a basic amino acid according to claim 9, wherein a $NH_4^+$-cation exchange resin is used.

11. The method for separating a basic amino acid according to claim 1, wherein said eluting agent is 4N ammonia water.

12. The method for separating a basic amino acid according to claim 1, wherein a single tower adsorption-elution system is used.

13. The method for separating a basic amino acid according to claim 1, wherein a 4-tower adsorption and 3-tower elution system is used.

* * * * *